United States Patent [19]

Krespan et al.

[11] Patent Number: 4,935,558
[45] Date of Patent: Jun. 19, 1990

[54] REDUCTIVE DECHLORINATION OF 1,1,1,2-TETRAFLUORO-2-CHLOROETHANE

[75] Inventors: Carl G. Krespan; Leo E. Manzer, both of Wilmington, Del.

[73] Assignee: E. I. du Pont de Nemours and Company, Wilmington, Del.

[21] Appl. No.: 301,380

[22] Filed: Jan. 25, 1989

[51] Int. Cl.$^5$ .................... C07C 17/24; C07C 17/36; C07C 19/02
[52] U.S. Cl. .................................. 570/176; 570/179
[58] Field of Search ......................................... 570/176

[56] References Cited

U.S. PATENT DOCUMENTS 2,920,112 1/1960 Larsen .................................. 570/176
4,745,237 5/1988 Ballard et al. ....................... 570/176

FOREIGN PATENT DOCUMENTS 164954 12/1985 European Pat. Off. ............ 570/176
58-222038 12/1983 Japan .

*Primary Examiner*—J. E. Evans

[57] ABSTRACT

A process for the preparation of 1,1,1,2-tetrafluoroethane by reacting 1,1,1,2-tetrafluoro-2-chloroethane in a polar aprotic solvent with zinc in the presence of a proton source at a temperature from about 65° C. to about 250° C.

18 Claims, No Drawings

REDUCTIVE DECHLORINATION OF 1,1,1,2-TETRAFLUORO-2-CHLOROETHANE

FIELD OF THE INVENTION

Process for the preparation of 1,1,1,2-tetrafluoroethane by the reductive dechlorination of 1,1,2-tetrafluoro-2-chloroethane.

BACKGROUND OF THE INVENTION

Reductive dechlorinations utilizing elemental metal in a protic solvent are known in the art, but are generally ineffective in preparing fluorohydrocarbons, i.e., a compound containing only fluorine, hydrogen, and carbon.

J No. 58,222,038 discloses a process for the preparation of 1,1,1-trifluoro-2,2-dichloroethane by reduction of 1,1,1-trifluoro-2,2,2-trichloroethane with zinc in a protic solvent.

U.S. Pat. No. 4,745,237 discloses a process for the preparation of 1,1,1,2-tetrafluoro-2-chloroethane from 1,1,1,2-tetrafluoro-2,2-dichloroethane by reaction with alkali metal amalgam in an active hydrogen containing medium, e.g. methanol and water.

There is growing demand for environmentally desirable fluorocarbons for use as solvents, blowing agents and, particularly, refrigerants. One suitable fluorocarbon particularly useful as a refrigerant is 1,1,1,2-tetrafluoroethane. This invention provides a process for producing 1,1,1,2-tetrafluoroethane by reductive chlorination.

SUMMARY OF THE INVENTION

This invention provides a process for the preparation of 1,1,1,2-tetrafluoroethane by reacting 1,1,1,2-tetrafluoro-2-chloroethane in a polar aprotic solvent with zinc in the presence of a proton source at a temperature from about 65° C. to about 250° C.

DETAILS OF THE INVENTION

Polar aprotic solvents useful in the practice of this invention are well known in the art and include dimethylformamide, dimethylacetamide, $CH_3CN$, $C_6H_5CN$, dimethoxyethane, tetraethylene glycol dimethyl ether, tetrahydrofuran, adiponitrile, and N-methylpyrrolidinone.

The zinc useful in the practice of this invention is elemental or metallic zinc, preferably in finely divided form.

Proton sources useful in the practice of this invention include water, HCl, alcohols, carboxylic acids, ammonium carboxylates, ammonium halides, and ammonium sulfates. Of this list of proton sources, water and alcohols are least preferred due to relatively lower acidity. For optimum availability and economy the preferred alcohols are selected from branched or straight chain alcohols having from 1 to 4 carbon atoms. In general the carboxylic acids can be branched or straight chain alkyls, cycloalkyls or aryls having from 1 to 8 carbon atoms. For the same reasons, the preferred carboxylic acids are selected from branched or straight chain carboxylic acids having from 1 to 4 carbon atoms. The ammonium component of the proton sources listed above is of the formula $NR_3H^+$, wherein R is at least one selected from hydrogen, an alkyl having from 1 to 4 carbon atoms, and substituted or unsubstituted pyridinium. Pyridinium is preferred for economy and stability. The carboxylate component of the proton sources listed above can be a branched or straight chain alkyl, cycloalkyl or aryl having from 1 to 8 carbon atoms. Benzoate and acetate are preferred for economy and stability.

For optimum yield and convenience, a temperature of about 100° C. to about 200° C. is preferred.

Pressure is not particularly critical in the practice of this invention. Pressures from 1 atm. to 200 atm. can be used, with pressures equal to or greater than 10 atm. being preferred.

The reaction time varies somewhat with reaction temperature and the polar aprotic solvent chosen, but will generally be from 5 minutes to 20 hours.

The reaction vessel utilized in the practice of this invention is not critical. Any reaction vessel capable of withstanding the chosen pressure can be used. Metal reaction vessels are preferred for convenience and pressure tolerance. It is preferred that the reaction vessel be equipped with some form of agitation device to insure mixing of the elemental zinc and optimum conversion.

The 1,1,1,2-tetrafluoroethane prepared in accordance with this invention can easily be isolated by fractional distillation of the reaction products.

EXAMPLES

In the following illustrative examples, all parts and percentages are by weight and all temperatures are Centigrade unless otherwise stated. All reactions use commercially available starting materials.

EXAMPLE 1

A mixture of 3.3 grams (0.05 mol) of zinc dust, 60 mL of dimethylformamide, 27.8 grams (0.20 mol) of pyridinium acetate, and 14 grams (0.10 mol) of 1,1,1,2-tetrafluoro-2-chloroethane was heated in a 240 mL metal tube at 140° for 15 hours. During this time the pressure increased from 10 atm. to 28 atm. Volatile materials were driven off by heating the reaction mixture at 125°, affording 8.1 grams of a product mixture which was analyzed by Gas Chromatograph/Mass Spectrometer. The product mixture consisted essentially of 0.42 grams (4% conversion, 9% yield) of 1,1,1,2-tetrafluoroethane, 7.38 grams (53% recovery) of unreacted 1,1,1,2-tetrafluoro-2-chloroethane, 0.02 grams (0.2% conversion, 0.5% yield) of trifluoroethylene, the remainder consisting of other fluorinated by products. The selectivity of 1,1,1,2-tetrafluoroethane versus trifluoromethylene is 20:1.

EXAMPLE 2

The procedure of Example 1 was followed except that the pyridinium acetate was replaced with 20 mL of water. The volatile product mixture, 4.9 grams, consisted essentially of 4.8 grams (34% recovery of unreacted 1,1,1,2-tetrafluoro-2-chloroethane and 0.08 grams (1% conversion, 1% yield) of 1,1,1,2-tetrafluoroethane, chloroethane, along with only a trace of trifluoroethylene.

CONTROL 1

The procedure of Example 1 was followed except that the dimethylformamide was replaced by 60 mL of absolute ethanol. The product mixture, 17.9 grams, consisted primarily of ethanol and unreacted 1,1,1,2-tetrafluoro-2-chloroethane with only 0.06 grams (<1% conversion) of 1,1,1,2-tetrafluoroethane and only a trace of trifluoroethylene.

What is claimed:

1. A process for the preparation of 1,1,1,2-tetrafluoroethane by reacting 1,1,1,2-tetrafluoro-2-chloroethane in a polar aprotic solvent with zinc in the presence of a proton source at a temperature from about 65° C. to about 250° C.

2. The process of claim 1 wherein the temperature is from about 100° C. to about 200° C.

3. The process of claim 1 wherein the polar aprotic solvent is at least one selected from dimethylformamide, dimethylacetamide, $CH_3CN$, $C_6H_5CN$, dimethoxyethane, tetraethylene glycol dimethyl ether, tetrahydrofuran, adiponitrile, and N-methylpyrrolidinone.

4. The process of claim 1 wherein the proton source is at least one selected from water, HCl, alcohols, carboxylic acids, ammonium carboxylates, ammonium halides, and ammonium sulfates.

5. The process of claim 4 wherein the proton source is at least one selected from HCl, carboxylic acids, ammonium carboxylates, ammonium halides, and ammonium sulfates.

6. The process of claim 3 wherein the proton source is at least one selected from HCl, carboxylic acids, ammonium carboxylates, ammonium halides, and ammonium sulfates.

7. The process of claim 6 wherein the temperature is from about 100° C. to about 200° C.

8. The process of claim 7 wherein the pressure is from about 10 atmospheres to about 200 atmospheres.

9. The process of claim 7 wherein the polar aprotic solvent comprises dimethylformamide.

10. The process of claim 3 wherein the proton source is selected from compounds having an ammonium component of the formula $NR_3H^+$ wherein the R groups are selected from hydrogen, alkyl groups having from 1 to 4 carbon atoms, or represent substituted or unsubstituted pyridinium.

11. The process of claim 10 wherein the proton source comprises pyridinium.

12. The process of claim 10 wherein the temperature is from about 100° C. to about 200° C.

13. The process of claim 12 wherein the pressure is from about 10 atmospheres to about 200 atmospheres.

14. The process of claim 13 wherein the polar aprotic solvent comprises dimethylformamide.

15. The process of claim 3 wherein the proton source comprises pyridinium acetate.

16. The process of claim 15 wherein the temperature is from about 100° C. to about 200° C.

17. The process of claim 16 wherein the pressure is from about 10 atmospheres to about 200 atmospheres.

18. The process of claim 17 wherein the polar aprotic solvent comprises dimethylformamide.

* * * * *